US006984246B2

(12) United States Patent
Huang

(10) Patent No.: US 6,984,246 B2
(45) Date of Patent: Jan. 10, 2006

(54) ARTIFICIAL INTERVERTEBRAL DISC FLEXIBLY ORIENTED BY SPRING-REINFORCED BELLOWS

(75) Inventor: Shih-Shing Huang, Taipei (TW)

(73) Assignee: Tain-Yew Shi, Taipei (TW)

( * ) Notice: Subject to any disclaimer, the term of this patent is extended or adjusted under 35 U.S.C. 154(b) by 163 days.

(21) Appl. No.: 10/861,835

(22) Filed: Jun. 5, 2004

(65) Prior Publication Data
US 2004/0249462 A1 Dec. 9, 2004

Related U.S. Application Data

(60) Provisional application No. 60/477,171, filed on Jun. 6, 2003.

(51) Int. Cl.
*A61F 2/44* (2006.01)
(52) U.S. Cl. ............................. 623/17.13; 623/17.12
(58) Field of Classification Search ............. 623/17.13, 623/17.11, 17.12, 17.15, 17.16, 23.41, 23.52
See application file for complete search history.

(56) References Cited

U.S. PATENT DOCUMENTS

| | | | | |
|---|---|---|---|---|
| 5,674,294 A | * | 10/1997 | Bainville et al. | 623/17.16 |
| 6,187,043 B1 | * | 2/2001 | Ledergerber | 623/8 |
| 6,264,695 B1 | * | 7/2001 | Stoy | 623/17.16 |
| 6,582,466 B1 | * | 6/2003 | Gauchet | 623/17.11 |

* cited by examiner

*Primary Examiner*—Eduardo C. Robert
*Assistant Examiner*—David Comstock

(57) ABSTRACT

An artificial intervertebral disc includes: an upper retaining member secured to an upper vertebra; a lower retaining member secured to a lower vertebra adjacent to the upper vertebra; and a nucleus member flexibly resiliently formed between the upper and the lower retaining members having at least an outer and an inner bellows each reinforced and integrally formed with a helical spring to define an outer annulus between the outer and inner bellows and a core formed within the inner bellows.

7 Claims, 2 Drawing Sheets

ARTIFICIAL INTERVERTEBRAL DISC FLEXIBLY ORIENTED BY SPRING-REINFORCED BELLOWS

This application claims the benefit of U.S. Provisional Ser. No. 60/477,171 filed Jun. 6, 2003.

BACKGROUND OF THE INVENTION

U.S. Pat. No. 6,533,818 to Weber et al. disclosed an artificial spinal disc including a top and bottom layer fused to the vertebrae and a middle layer formed with polymer having mechanical properties similar to a natural spinal disc.

However, such a prior art has the following drawbacks:
1. The middle layer is made of compressible polymer. Its supporting strength to retain the adjacent vertebrae is doubtful.
2. If the outer support (65) is made of high-strength polymer to increase the supporting strength of the artificial disc, the flexibility of the disc will then become poorer.
3. The polymer layer is fixedly formed between the top and bottom layers between the adjacent vertebrae. It is not suitable to be an implant for minimally invasive surgery.

The present inventor has found the drawbacks of the conventional artificial spinal disc and invented the present artificial intervertebral disc better than the prior art.

SUMMARY OF THE INVENTION

The object of the present invention is to provide an artificial intervertebral disc including: an upper retaining member secured to an upper vertebra; a lower retaining member secured to a lower vertebra adjacent to the upper vertebra; and a nucleus member flexibly resiliently formed between the upper and the lower retaining members having at least an outer and an inner bellows each reinforced and integrally formed with a helical spring to define an outer annulus between the outer and inner bellows and a core formed within the inner bellows, thereby providing an artificial intervertebral disc having nice flexibility and supporting strength to vividly simulate a natural spinal disc.

DETAILED DESCRIPTION

Figure 1:
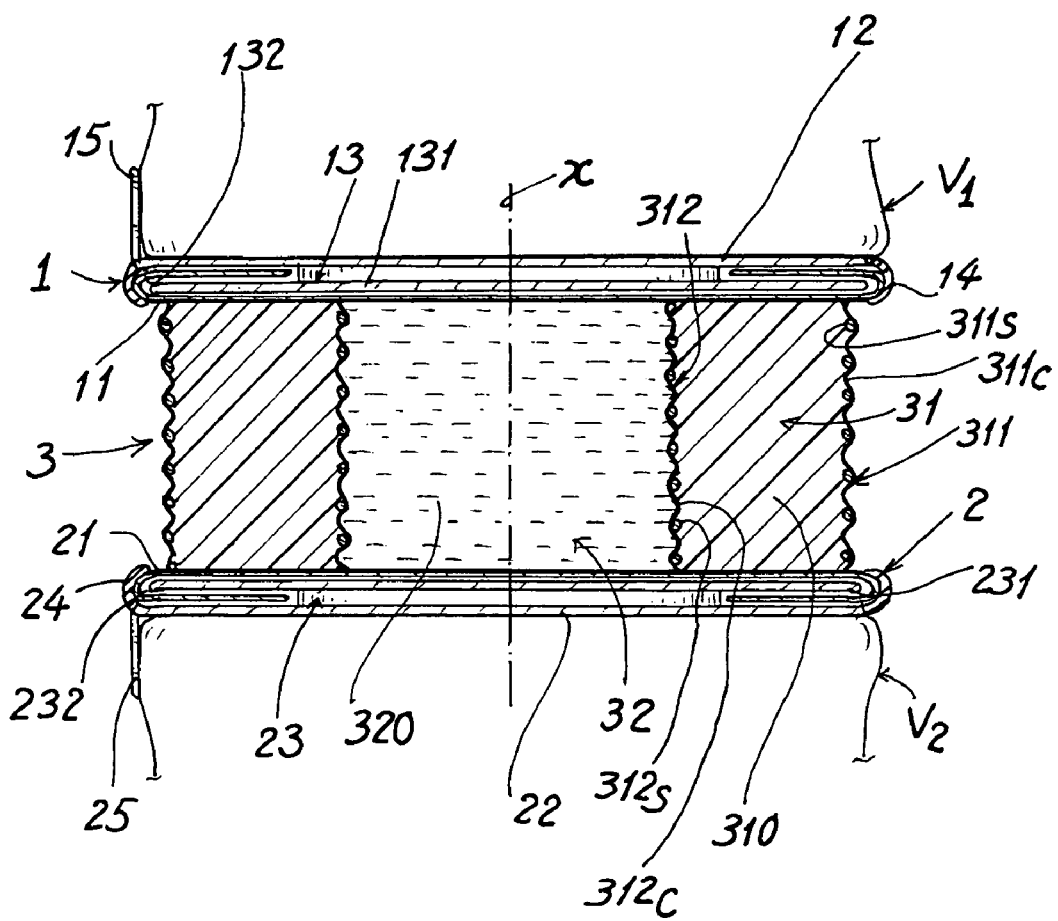
FIG. 1 is a sectional drawing of the present invention.
Figure 2:
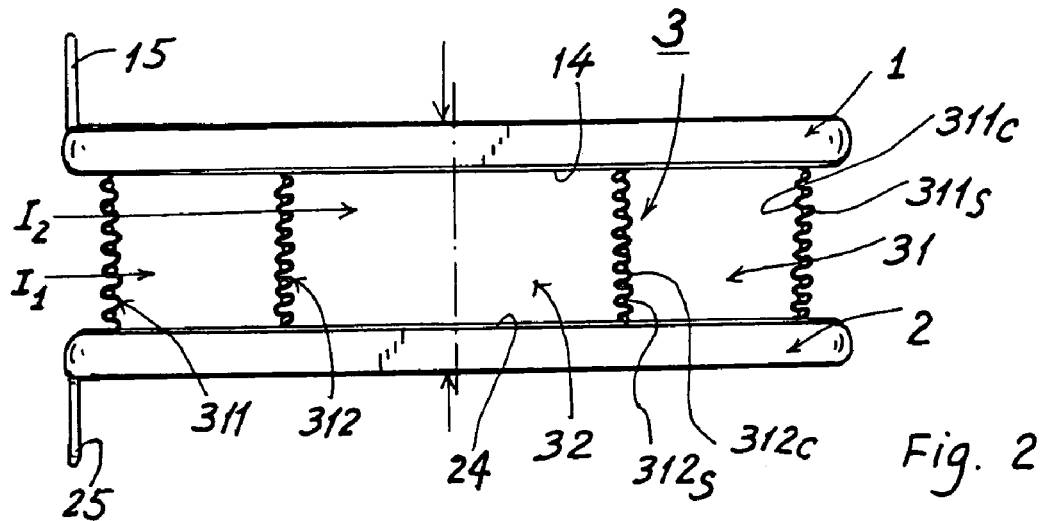
FIG. 2 is an illustration of the present invention when compressed before being filled.
Figure 3:
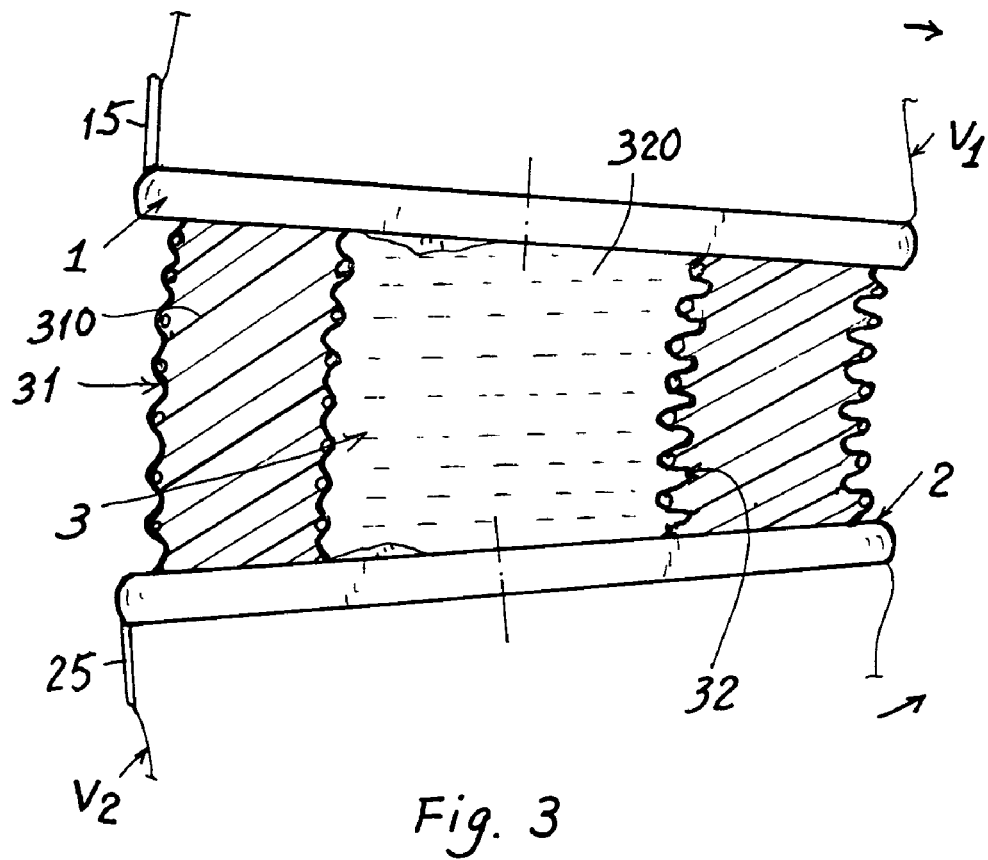
FIG. 3 shows a tilted situation of the present invention as retained between flexibly bent vertebrae.

As shown in FIGS. 1~3, the artificial intervertebral disc of the present invention comprises: an upper retaining member 1 secured to an upper vertebra $V_1$; a lower retaining member 2 secured to a lower vertebra $V_2$ adjacent to the upper vertebra $V_1$; and a nucleus member 3 flexibly resiliently formed between the upper and the lower retaining members 1, 2.

The nucleus member 3 includes: an outer annulus 31 annularly defined between an outer bellows 311 and an inner bellows 312 and having a relatively hard outer cushioning filler 310 filled in the outer annulus 31 to mimic the annulus fibrosus of a natural spinal disc; and a core 32 defined within the inner bellows 312 and having a relatively soft inner cushioning filler 320 filled in the core 32 to mimic the nucleus pulposus of a natural spinal disc.

The outer bellows 311 includes: a helical spring 311s integrally formed with a flexible cover 311c to encase the outer filler 310 therein.

The helical spring 311s may be made of plastic spring such as carbon-fiber reinforced plastic or other resilient materials.

The flexible (or helical) cover 311c may be made of high strength polymer such as polyurethane reinforced with reinforcing materials therein.

The inner bellows 312 is similar to the outer bellows 311, and includes: a helical spring 312s integrally formed with a flexible (or helical) cover 312c.

The relatively hard outer cushioning filler 310 may be selected from: high-density or high-hardness elastomers, foams, gels and fluids; while the relatively soft inner cushioning filler 320 may be selected from: low-density or low-hardness elastomers, foams, gels and fluids.

The outer cushioning filler 310 may be selected from polyurethane, which may be preformed in the outer annulus 31. Or, the polyurethane may be a two-component system and be injected into the annulus 31 of the nucleus member 3 which is previously compressed or squeezed when implanted and inserted in between two adjacent vertebrae as shown in FIG. 2 for minimally invasive surgery. After injection, the polyurethane will be foaming in situ to expandibly form a shock-absorbable cushioning member of the present invention. The inner filler 320 may be simultaneously injected into the core 32.

The outer cushioning filler 310 such as made of high-density polyurethane will provide the supporting strength for the adjacent vertebrae $V_1$, $V_2$; while the inner cushioning filler 320 filled with low-density (low-hardness) PU or silicon elastomer, gel or foam therein will render better shock absorbing property to reliably play the disc role in between the vertebrae.

Each bellows 311 or 312, as produced by integrally forming a helical spring with a helical cover, will play an important role in this invention to render several advantages to be superior to the prior arts, namely:
1. The helical spring 311s or 312s will auxiliarily provide the supporting strength in cooperation with the fillers for stably retaining the vertebrae.
2. The bellows 311, 312 will provide a better flexibility for the vertebrae. The bellows will especially help a smooth bending of the vertebrae (FIG. 3).
3. The bellows 311, 312 may be squeezed or compressed for an easy insertion in between adjacent vertebrae $V_1$, $V_2$ and then respectively injected with fillers 310, 320 as numerals $I_1$, $I_2$ as shown in FIG. 2 to thereby be suitable for minimally invasive surgery.
4. Each bellows is formed by integrally forming a helical spring and a flexible cover, in which the helical spring will serve as a reinforcing rib (or rod) of the flexible cover. After integral forming with the elastomer (e.g. P.U.) of the filler 310, the spring will strongly reinforce the filler 310 and the cover of the bellows, like the steel of a reinforcing concrete (RC), to thereby increase the strength of the artificial disc to prevent from bulge or burst of the nucleus and to prolong the service life of the disc.

Each retaining member 1 or 2 may be directly secured to each vertebra $V_1$ or $V_2$; or may be rotatably coupled to either vertebra as illustrated in FIG. 1.

The upper retaining member 1 includes: a substrate plate 11 for firmly forming or fixing the bellows 311, 312 on the substrate plate 11 and for encapsulating the fillers 310, 320 within the bellows 311, 312 and the substrate plate 11 in cooperation with the lower retaining member 2; a fusion plate 12 rotatably engaging with the substrate plate 11 by a coupling 13 and secured to the upper vertebra $V_1$ by fusion or bone ingrowth (in which a biodegradable composition is preferably coated on the fusion plate 12), a sealing flap 14 rotatably engaging with an outer periphery of the substrate plate 11 for precluding the intrusion of unexpected body liquid or organic matters into the coupling 13, and at least a lug 15 formed on the fusion plate 12 adapted to be fixed to the vertebra $V_1$ by bolts.

The coupling 13 includes: a rotor member (or a "ball") 131 protruding from the fusion plate 12, and a socket 132 recessed in the substrate plate 11 and rotatably engaging with the rotor member 131, thereby rotatably coupling the upper vertebra $V_1$ with the nucleus member 3 and allowing a relative rotation of the vertebra $V_1$ with the artificial disc of this invention.

The lower retaining member 2 includes: a substrate plate 21 for firmly forming or fixing the bellows 311, 312 on the substrate plate 21 and for encapsulating the fillers 310, 320 within the bellows 311, 312 and the substrate plate 21 in cooperation with the upper retaining member 1; a fusion plate 22 rotatably engaging with the substrate plate 21 by a coupling 23 and secured to the lower vertebra $V_2$ by fusion or bone ingrowth, a sealing flap 24 rotatably engaging with an outer periphery of the substrate plate 21 for precluding the intrusion of unexpected body liquid or organic matters into the coupling 23, and at least a lug 25 formed on the fusion plate 22 adapted to be fixed to the vertebra $V_2$ by bolts.

The coupling 23 includes: a rotor member (or a "ball") 231 protruding from the fusion plate 22, and a socket 232 recessed in the substrate plate 21 and rotatably engaging with the rotor member 231, thereby rotatably coupling the lower vertebra $V_2$ with the nucleus member 3 and allowing a relative rotation of the vertebra $V_2$ with the artificial disc of this invention.

By the way, the disc may be rotatably coupled to the vertebrae $V_1$, $V_2$ for a smooth rotatable movements of the adjacent vertebrae.

A bio-compatible lubricant or fluid may be added into the revolving parts such as the couplings 13, 23 of the present invention to enhance a smooth manipulation.

The two bellows 311, 312 may be concentric about a longitudinal axis X formed at a longitudinal center of the disc of the present invention.

For further enhancing the supporting strength of the present invention, a further bellows (not shown) may be formed in the core 32.

The present invention may be further modified without departing from the spirit and scope of the present invention.

I claim:
1. An artificial intervertebral disc comprising:
   an upper retaining member adapted to be secured to an upper vertebra;
   a lower retaining member adapted to be secured to a lower vertebra adjacent to the upper vertebra; and
   a nucleus member flexibly resiliently formed between said upper and lower retaining members; and said nucleus member including:
   an outer annulus annularly defined between an outer bellows and an inner bellows, and a core defined within the inner bellows;
   said outer and inner bellows respectively formed between said upper and lower retaining members; said outer annulus having a relatively hard outer cushioning filler filled or formed in the annulus and said core having a relative soft inner cushioning filler filled or formed in the core; and wherein each said bellows including: a helical spring and a flexible cover integrally formed with said helical spring.

2. A disc according to claim 1, wherein said outer cushioning filler is selected from the group consisting of: high-density or high-hardness elastomers, foams, gels and fluids.

3. A disc according to claim 1, wherein said inner cushioning filler is selected from the group consisting of: low-density or low-hardness elastomers, foams, gels and fluids.

4. A disc according to claim 1, wherein said nucleus member is formed by respectively injecting said outer and inner cushioning fillers into said annulus and said core of said nucleus member, which is previously compressed and inserted in between adjacent vertebrae, adapted for minimally invasive surgery.

5. A disc according to claim 1, wherein said outer cushioning filler is a foaming material foaming in situ in said annulus when the disc is inserted in between adjacent vertebrae.

6. A disc according to claim 1, wherein each said retaining member includes: a substrate plate for firmly fixing the bellows on the substrate plate and for encapsulating the fillers within the bellows and the substrate plate in cooperation with the other said retaining member; a fusion plate rotatably engaging with the substrate plate by a coupling and secured to one said vertebra, a sealing flap rotatably engaging with an outer periphery of the substrate plate for precluding the intrusion of unexpected liquid or matters into the coupling, and at least a lug formed on the fusion plate adapted to be fixed to one said vertebra.

7. A disc according to claim 6, wherein said coupling includes: a rotor member protruding from the fusion plate, and a socket recessed in the substrate plate and rotatably engaging with the rotor member.

* * * * *